United States Patent [19]

Drbal et al.

[11] 4,276,260

[45] Jun. 30, 1981

[54] FLUID TRANSFER MECHANISM

[75] Inventors: Vladimir J. Drbal, Hollywood; Guenter Ginsberg, Miami; Bruce J. Hodgins, Hialeah, all of Fla.; John A. Richardson, Shirley, Mass.; Ted W. Britton, Opa Locka, Fla.; Richard M. Grimm, Zolfo Springs, Fla.; Ernesto Bello, Miami Springs, Fla.; Rodolfo R. Rodriguez, Miami, Fla.; Ivan K. Saltz, Cooper City, Fla.

[73] Assignee: Coulter Electronics, Inc., Hialeah, Fla.

[21] Appl. No.: 115,691

[22] Filed: Jan. 28, 1980

[51] Int. Cl.³ .............................................. G01N 1/14
[52] U.S. Cl. .................................. 422/100; 73/864.25; 141/130; 422/63; 422/64
[58] Field of Search ................... 422/100, 64, 63; 73/425.6, 423 A; 141/130, 198

[56] References Cited

U.S. PATENT DOCUMENTS

| 3,252,330 | 5/1966 | Kling | 422/100 X |
| 3,576,605 | 4/1971 | Drake et al. | 422/100 X |
| 3,635,094 | 1/1972 | Oberli | 73/423 A |
| 4,076,503 | 2/1978 | Atwood et al. | 422/100 |
| 4,131,426 | 12/1978 | Range | 422/100 |

Primary Examiner—Ronald Serwin
Attorney, Agent, or Firm—Silverman, Cass & Singer, Ltd.

[57] ABSTRACT

A fluid transfer mechanism for rapidly and accurately picking up or aspirating a fluid quantity or aliquot in one position, moving it to a second position and dispensing the aspirated aliquot. The mechanism includes an arm mounted on a high helix shaft on one end and driven up and down the shaft by a first motor and rotated around the shaft by a second motor. The arm includes at a second end a fluid transfer probe which is moved into and out of the fluids to aspirate and dispense the fluids in precise angular locations. The arm may be accelerated and deaccelerated as it is rotated to avoid vibrations and spilling of the fluid from the probe. The probe may include a level sensing structure for sensing when the probe has contacted a fluid surface. The probe also may be coupled to an oscillator to oscillate the probe in a vessel into which the fluid has been dispensed to mix the fluids therein.

19 Claims, 8 Drawing Figures

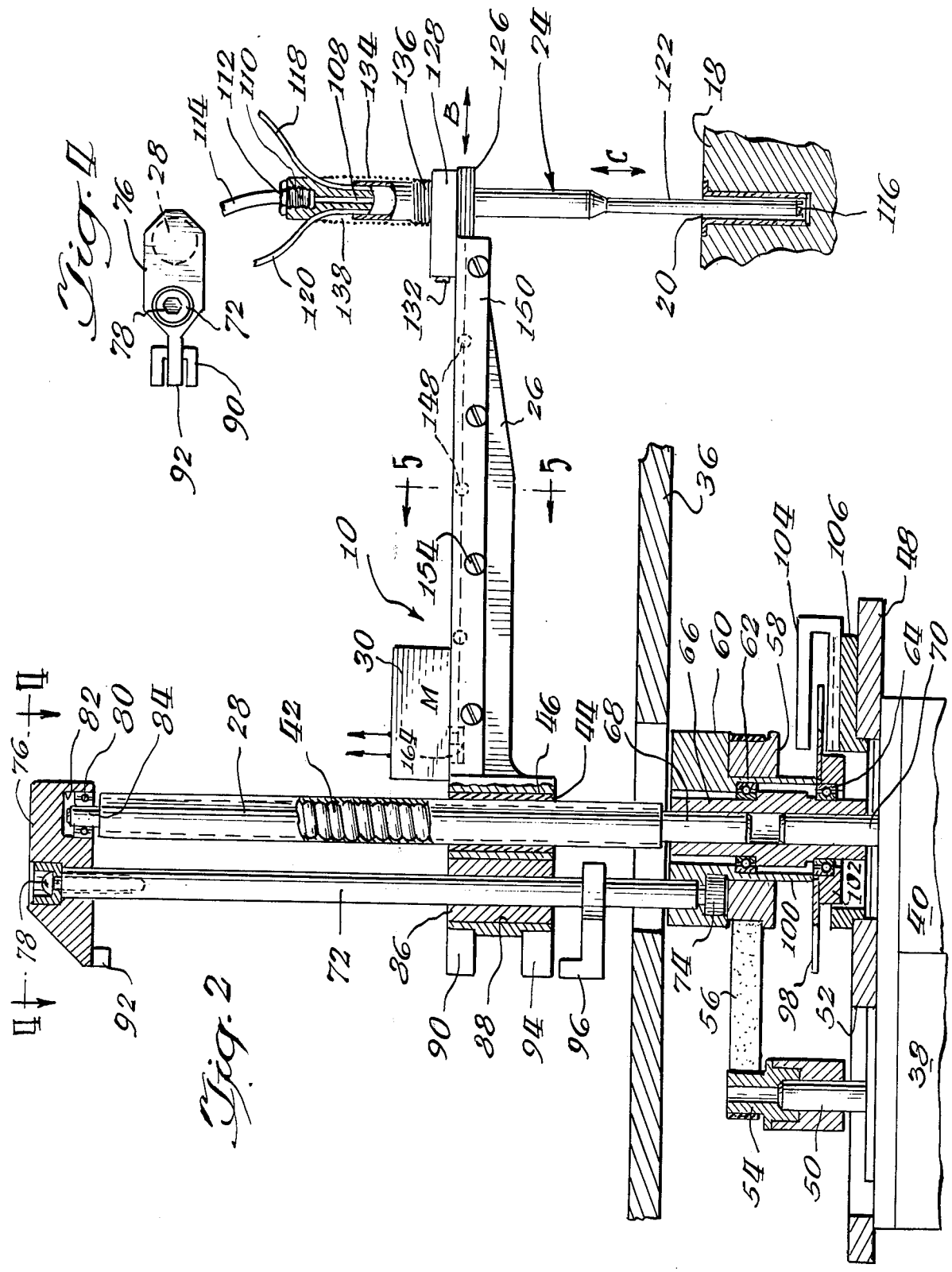

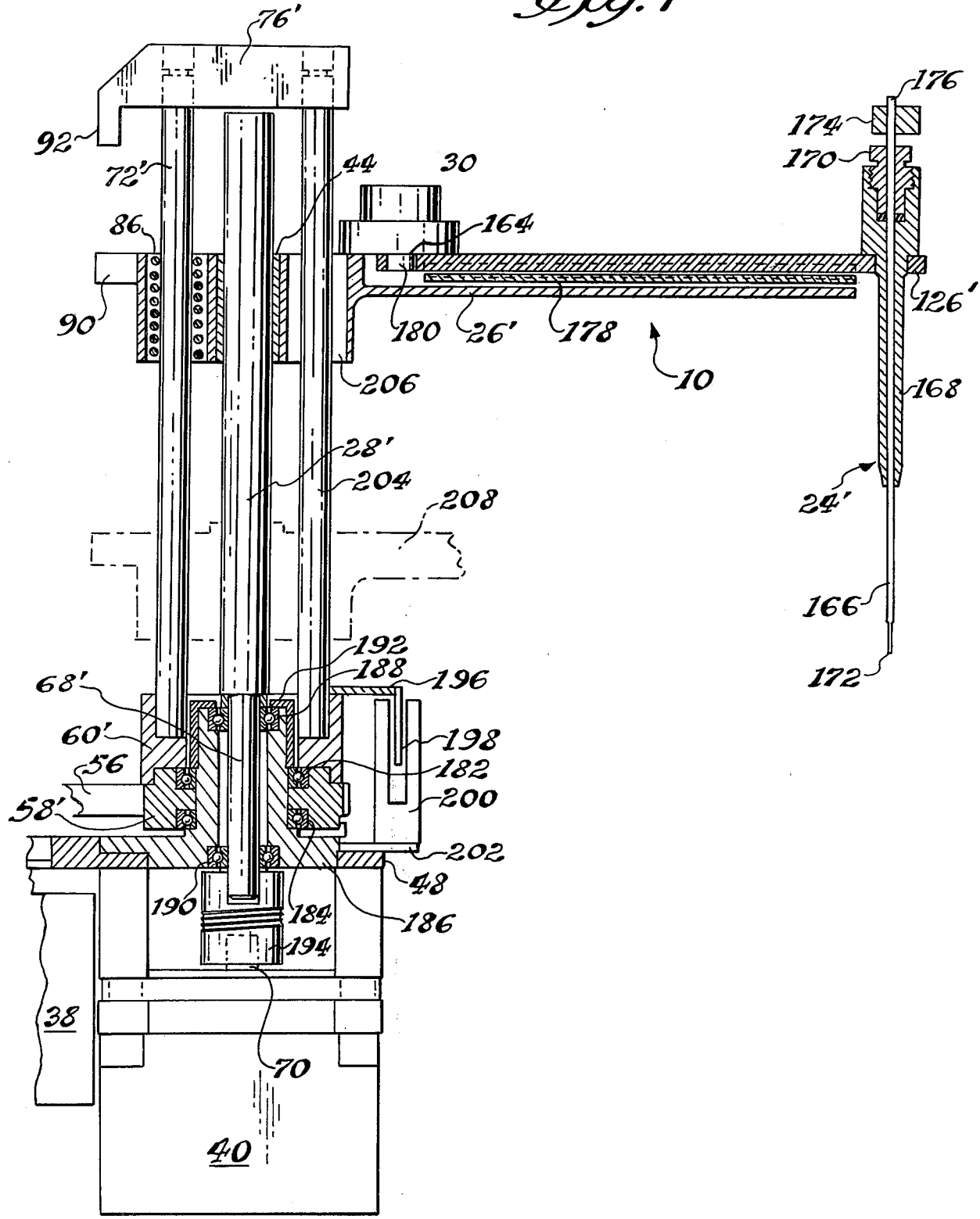

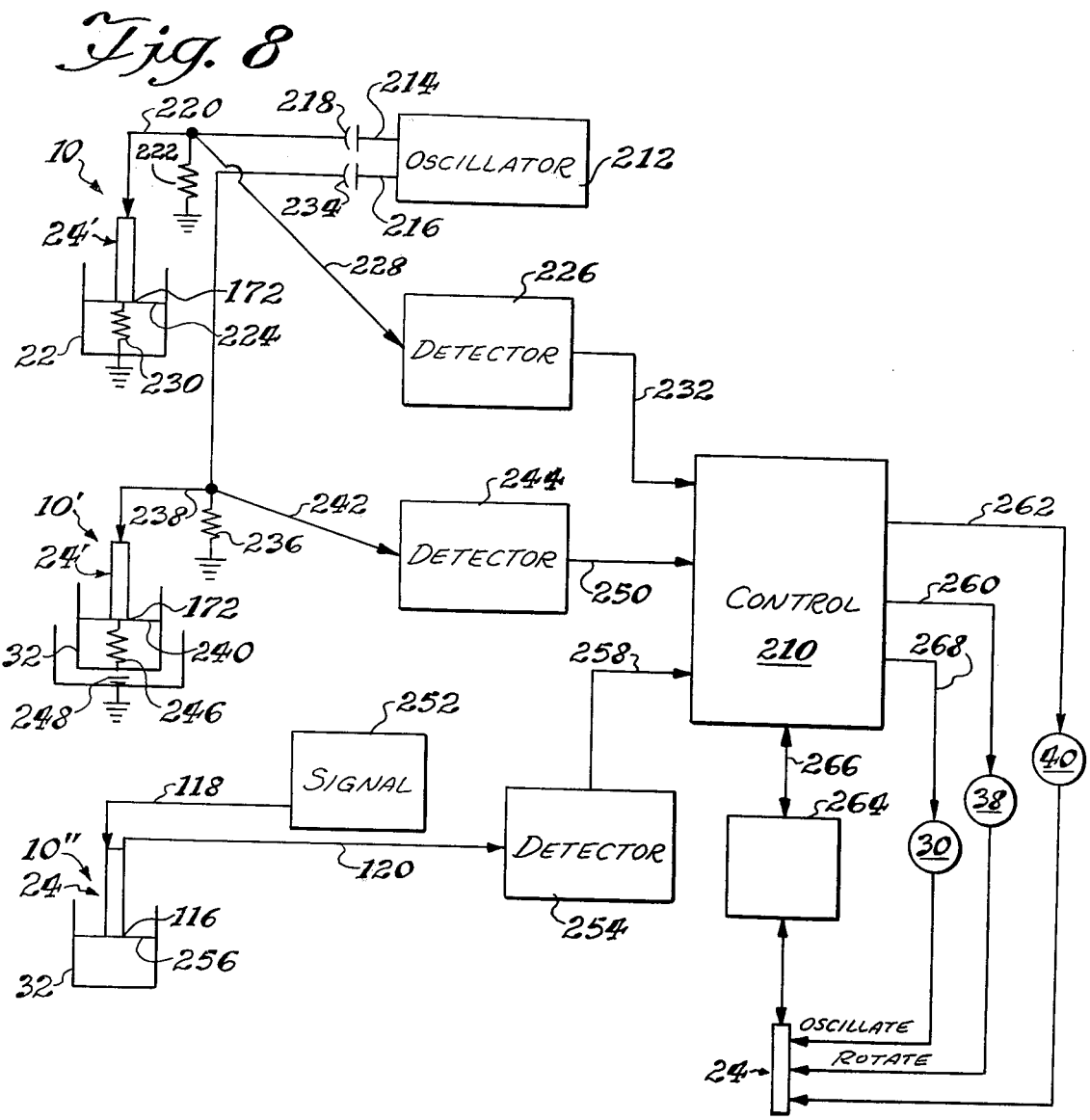

FLUID TRANSFER MECHANISM

CROSS REFERENCE TO RELATED APPLICATIONS

This invention is related to the subject matter disclosed in the following copending and commonly assigned applications which are incorporated herein by reference:

Apparatus For Monitoring Chemical Reactions and Employing Moving Photometer Means, G. Ginsberg et al, Ser. No. 846,337, filed Oct. 28, 1977, now allowed.

Sample and Stat Feeding System and Sample Tray, G. Ginsberg et al, Attorney Docket No. 177101 Case 2W, Ser. No. 115,294, filed Jan. 28, 1980 filed concurrently herewith.

Cuvette Washing Apparatus, B. Hodgins, Ser. No. 115,692, filed Jan. 28, 1980, filed concurrently herewith.

System and Program for Chemical Reaction Observation with a Moving Photometer, G. Ginsberg et al, Ser. No. 115,734, filed Jan. 28, 1980, filed concurrently herewith.

Probe Washer, B. Hodgins, Attorney Docket No. Ser. No. 115,625, filed Jan. 28, 1980, filed concurrently herewith.

Variable Stop Syringe, B. Hodgins et al, Ser. No. 115,624, filed Jan. 28, 1980, filed concurrently herewith.

BACKGROUND OF THE INVENTION

The invention relates to a fluid transfer mechanism for picking up, transferring and dispensing fluid volumes and more particularly this invention concerns aspirating a fluid volume in a first position, rotating the aspirated fluid to a second position and dispensing the fluid volume in the second position.

Fluid transfer and dispensing mechanisms each operate to dispense amounts of fluid in a desired location; however, prior art devices do not have the capability to pick up on aspirate a precise fluid quantity in a first position, move the fluid quantity to a second position at a high rate of speed and with a very precise positioning of the fluid pick up and dispensing probe in the vertical and horizontal positions. Further, many of the prior art devices were developed to pump a dedicated fluid through the dispenser, such as reagents in chemical analyzing systems or to pick up multiple volumes in a fluid probe separated by air or other fluids. If the flexibility is desired to pick up and dispense different fluid quantities from different sources and mix them with other fluids then the dedicated or in line systems are not capable of being utilized since they either are physically connected only to one fluid or would run the risk of carry-over and contamination between fluids.

In some chemical analyzing systems sample fluids related to a particular patient are programmed for one or more analytical tests such as measuring the chemical reaction resulting from the addition of one or more reagents from a reagent supply. One disadvantage in prior art devices is caused by dedicated reagent positions and typically a dedicated reagent dispensing mechanism for each position. Generally the array of cuvettes or reaction vessels is segmented or divided into the number of positions required by the dedicated reagent positions. For example, 100 cuvette positions with 10 reagent positions results in samples from only 10 patients being tested in the system without regard to the number of tests conducted on the sample from each patient.

Patient No. 1 might require only one test, but all ten positions have to be allotted for that patient's sample in the device since each of the reagent positions is dedicated. Each of the nine empty positions may not be utilized so that the 100 position machine only is effective as a ten patient or sample machine. If this problem is doubled by including 10 second reagents, then the 100 position machine would be divided in half again such that samples from only five patients could be analyzed on the machine at one time. This results in a great increase in elapsed time for a given through put as well as a corresponding decrease in the efficiency of the system. It would be desirable to provide a fluid transfer mechanism which may pick up, move and dispense samples and reagents from one or more positions to increase the flexibility of the system so that each cuvette may include a sample and reagent fluid without regard to the number of tests or reagents in the system.

SUMMARY OF THE INVENTION

The above and other disadvantages of prior art fluid aspirating, transferring and dispensing systems and techniques are overcome in accordance with the present invention by providing a fluid transfer mechanism having an arm carrying a fluid probe on its distal end rotated about a fixed axis and precisely positionable in any vertical or horizontal position desired. The probe may include a level sensing mechanism for sensing when the probe contacts a fluid surface, an oscillating mechanism to oscillate the probe in a fluid vessel to stir the fluids in contact therewith as well as a control for accelerating and deaccelerating the rotational movement of the arm to avoid spillage from the fluid probe.

BRIEF DESCRIPTION OF THE DRAWINGS

FIG. 2 is a side plan view partially in section of one embodiment of the transfer mechanism;

FIG. 4 is a top view taken along the line 4—4 in FIG. 2;

FIG. 7 is a side plan view partially sectional of a second embodiment of the transfer mechanism; and FIG. 8 is a partial block and diagrammatical view of one control system of the fluid transfer mechanism.

DESCRIPTION OF THE PREFERRED EMBODIMENTS

Figures 1, 3:
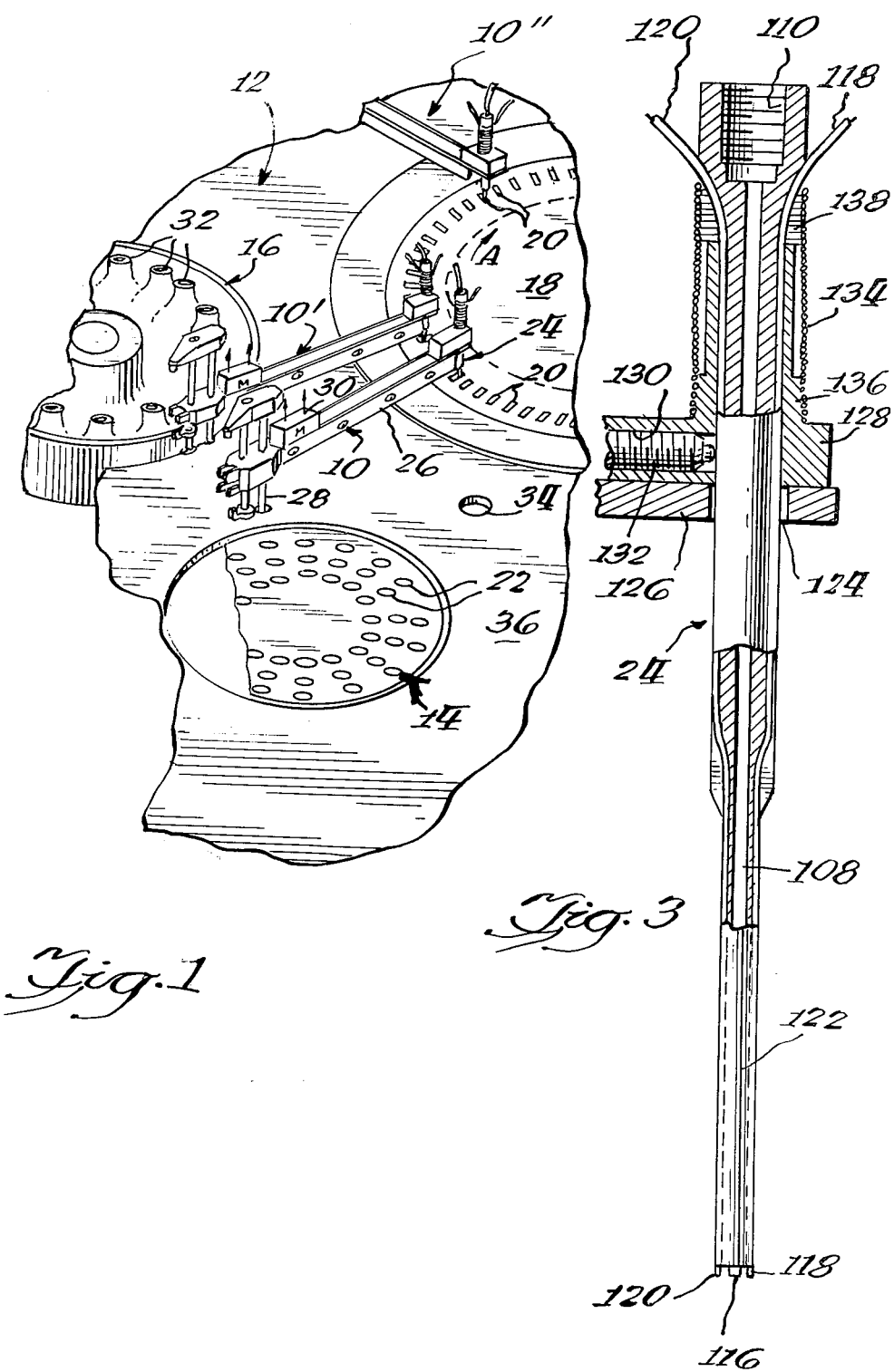
FIG. 1 is a partial perspective view of the fluid transfer mechanism of the invention and a partial perspective view of a chemical analyzer.
FIG. 3 is an enlarged side plan view partially in section of one embodiment of fluid probe of the mechanism.

Referring now to FIG. 1, a fluid transfer mechanism constructed in accordance with the invention is designated generally by the reference character 10. Three of the transfer mechanisms 10, 10' and 10" are illustrated in operation with a chemical reaction analyzer 12. The analyzer 12 may include a sample supply 14 and a reagent supply 16. The transfer mechanism 10 may be utilized with any type of analyzing or mixing system in which it is desirable to utilize the capabilities of the mechanism 10, as described hereinafter. For ease of description of the operations of the mechanism 10 and the flexibility inherent therein, one particular analyzer 12 will be described.

The analyzer 12 includes a cuvette rotor 18 which includes a plurality of cuvettes or cuvette cavities 20. The sample aliquots are picked up or aspirated by the mechanism 10 from the sample supply 14 and moved to and dispensed in the cuvettes 20. The sample aliquots are mixed with reagent aliquots which are picked up and dispensed by the mechanism 10' from the supply 16 for a first reagent. A second reagent may be added to the cuvettes 20 by the third mechanism 10'' from the supply 16 or from a different supply (not shown). The sample supply 14 may include samples, stats, controls and blanks which are picked up from the sample supply 14 in a predetermined order and which then are analyzed by the analyzer 12 in the cuvettes 20. The cuvettes 20 preferably are a renewable supply by being cleaned in the analyzer 12 before arriving again at the sample dispensing position of the mechanism 10.

The sample supply 14 has a plurality of cavities 22 in which the samples, blanks, stats, and controls may be placed and may include one or more pick up positions on an arc defined by a fluid probe 24. The cavities 22 may be moved to the pick up positions by rotating the supply 14. The probe 24 is rotated on an arm 26 about a shaft 28. The arm 26 is shown with the probe 24 in the dispensing position inserted into one of the cuvettes 20 in the rotor 18. The fluid picked up from the supply 14 will be dispensed and may be mixed by a motor 30 oscillating the probe 24 back and forth inside the cuvette 20. The mechanism 10' operates in a similar manner to pick up a fluid from one of a plurality of reagent containers 32 in the supply 16. The mechanism 10'' may pick up a second reagent quantity from the containers 32 or from another supply or row of containers (not shown).

The probe 24 is rotated about the shaft 28 and is vertically driven up and down on the shaft 28 to pick up and dispense the fluid quantities. The types of supplies as well as the cuvette array 20 are merely illustrative and the mechanisms 10, 10' and 10'' could pick up and dispense fluids from any position on an arc defined by the axis of the shaft 28. The fluids each may be different upon each operation of the mechanism 10 and it is very important that carry-over and contamination is eliminated since the fluids are related to tests upon the body fluids of a particular patient.

The operational positions of the mechanism 10 during each cycle will be as follows, describing the position of the probe 24 for simplicity. The probe 24 will be in a rest position such as above a probe washer 34 in which the probe is washed both internally and externally and dried at the end of each cycle in preparation for the next cycle. The probe 24 is first rotated to the proper pick up position above one of the cavities 22, driven downwardly into the cavity until it reaches the fluid, aspirates the precise aliquot of fluid desired, driven back up to the rotation position above the supply 14, rotated to a dispensing position above one of the cuvettes 20, driven downwardly into the cuvette 20, dispenses the aspirated fluid aliquot, oscillates to mix the fluids in the cuvette 20, driven upwardly to its rotating position, rotated to a position above the probe washer 34, driven down into the probe washer 34 wherein it is washed and dried of all previous fluids and then returned to its rest position above the probe washer 34. In one chemical analyzer 12, utilizing the above cycle, the cuvettes 20 are stepped by the rotor 18 one position in the direction "A" each six seconds and hence each of the mechanisms 10, 10' and 10'' performs each of the above movements in less than six seconds. It can be seen that it is extremely critical that each of the positions, both vertical and rotational, precisely and quickly must be attained by the probe 24.

A first embodiment of the transfer mechanism 10 and fluid probe 24 is illustrated in FIGS. 2 through 6. Referring to FIG. 2, the probe 24 is shown illustrated inserted in one of the cuvettes 20 in the rotor 18. The probe 24 is oscillated back and forth as shown by the arrow "B" to mix the fluids in the cuvette 20. The probe 24 is driven up and down along the axis of the shaft 28 as shown by the arrow "C" to remove and insert the probe into the cavities 22, cuvettes 20 and the probe washer 34. The mechanism 10 may be mounted to any convenient surface such as a baseplate 36 of the analyzer 12.

The arm 26 is mounted to the shaft 28 and is driven horizontally by a motor 38 and vertically by a motor 40. The motors 38 and 40, preferably are stepper motors to provide a very precise movement and alignment of the probe 24. In one example, the motor 38 moves the probe 24 along the horizontal arc two thousandths of an inch for each drive pulse it receives, while the motor 40 moves the probe 24 along the shaft 28 six thousandths of an inch for each pulse it receives. Further, the pulses may be applied to one or both of the motors 38 and 40 at an increasing and decreasing frequency to accelerate the probe 24 at the start of the movement to reach a high speed of movement and then deaccelerate so that the arm 26 does not stop suddenly and vibrate the probe 24 to spill fluids from the probe. This also is expedient, because of the number of motions the arm has to make in a very short period of time, plus the precision necessary for each of the locations of the probe 24.

To provide the speed and precision movements of the probe 24, the shaft 28 is a high helix screw having the pitch designed to provide the high speed movement necessary for the arm and probe movement. Only a portion 42 of the high helix screw thread is shown in detail; however, it will be understood that the threaded portion 42 extends from the uppermost potion of the shaft 28 to the lowermost portion of the shaft to which the arm 26 will be driven. The arm 26 is mounted to the shaft 28 by a high helix nut 44 of opposite configuration to the threads 42, which is engaged in a passageway 46 in the arm 26. The motors 38 and 40 may be mounted to a plate 48, which is below the baseplate 36 and may be mounted thereto or may be mounted to another surface.

The motor 38 includes a drive shaft 50 extending through an aperture or opening 52 in the plate 48 and has a pulley 54 mounted thereon. The pulley 54 has a drive belt engaged around one end. The belt 56 is engaged at the opposite end around drive pulley 58 mounted to a hub 60. The hub 60 is rotatingly mounted by a pair of bearings 62 and 64 around a screw drive shaft 66. The screw drive shaft 66 is pinned or or otherwise secured to a lower end 68 of the high helix screw 28 at one end and is pinned or otherwise secured at its opposite end to a drive shaft 70 of the motor 40.

The hub 60 also includes a guide rod 72 mounted or secured therein by a screw or other retaining device 74. The opposite end of the guide rod 72 is secured in an upper bearing retainer 76 by a screw or other securing device 78. The bearing retainer 76 includes a bearing 80 retained in a slot or recess 82. An upper end 84 of the helix 28 is rotatingly engaged in the bearing 80. The guide rod 72 maintains the angular position of the arm 26 by a bearing 86 mounted in the passageway 88 in the arm 26. The bearing 86 such as a ball bushing surrounds the guide rod 72 allowing the arm 26 to move easily up and down the rod 72, while accurately positioning the arm 26 and probe 24.

When the motor 40 is operated the screw shaft 28 is rotated driving the arm 26 and hence the probe 24 upwardly or downwardly by the drive nut 44. The bottom of the guide rod 72 is mounted in the hub 60, so that when the motor 38 is operated and the drive belt 56 rotates the hub 60, the guide rod 72 accurately will position the probe 24 as the hub 60 is rotated. The motor 40 may be operated in tandem with the motor 38 to maintain the position of the arm 26 on the shaft 28 if the positioning of the arm 26 on the shaft 28 is critical. If the arm 26 may be allowed to move slightly up and down as the arm is rotated by the motor 38, then the motor 40 need not be activated. Then as the hub 60 rotates around the shaft 28 the arm 26 will be driven slightly upwardly or downwardly on the shaft 28, since the nut 44 will be rotated on the threads 42 as the arm 26 is rotated by the guide rod 72.

The upward position of the arm 26 and the probe 24 may be ascertained by an optical reader 90 carried on the arm 26 which may be a conventional U or C shaped light switch, which will generate a signal when the light path between the arms is interrupted by a tab 92 depending from the upper bearing retainer 76 (best illustrated in FIG. 4). The lower position of the arm 26 and the probe 24 may be ascertained by a second optical switch 94 carried on the arm 26 below the switch 90 which is activated by a tab 96 mounted on the rod 72. The tabs 92 and 96 may be fixed or adjustable as desired to set the uppermost position as well as the lowermost position of the arm 26 and the probe 24.

The position defined by the tab 92 will be the uppermost position in which the probe 24 is removed from any of the vessels or cavities into which it may be placed so that it may be rotated without damage to the probe 24. The lowermost position defined by the tab 96 may be the lowermost position into which the probe 24 is inserted such as the desired spacing above the bottom of the cuvette 20 or in the probe washer 34. To provide the mechanism 10 with flexibility other tabs and readers could be utilized to define other positions, which readers could be mounted adjacent the reader 94 and have tabs extending vertically upwards parallel to the rod 72 and mounted to the rod 72 or hub 60.

The angular position of the arm 26 is determined by the horizontal drive motor 38 and may be verified by a code wheel 98 which is secured to a depending flange 100 of the hub 60 by a lower bearing holder 102. The code wheel 98 rotates with the hub 60 and the angular position of the code wheel 98 and hence the arm 26 and the probe 24 may be sensed by an optical reader 104 mounted to the plate 48 by a mounting block 106. The code wheel 98 may be utilized to determine the angular position of the probe 24 or it just may be utilized as a check to verify the position which has been determined by the number of drive pulses fed to the motor 40. Since each of the motors 38 and 40 preferably are stepper motors and are driven a precise distance for each drive pulse supplied thereto, the vertical and rotational position of the probe 24 may be determined merely by the number of pulses fed to the motors 38 and 40. Tabs 92 and 96 and the code wheel 98 then just may be utilized to verify the position determined by the drive motors.

The probe 24 is best illustrated in FIGS. 2 and 3 and includes a central passageway 108 which extends the length of the probe and opens at the top in a bore 110 into which may be fitted a fluid fitting 112 to which is connected a conventional fluid tubing 114. The passageway 108 preferably is formed in a non reactive plastic material and extends to and opens through a bottom end 116 which is the fluid aspirating and dispensing portion of the probe 24. The end 116 and a pair of electrical leads 118 and 120 extend out of a bottom non conductive sheath 122. The sheath 122 is dimensioned to fit within the inner dimensions of the cuvettes 20, the cavities 22 and the probe washer 34.

The upper ends of the leads 118 and 120 are coupled to a fluid sensing circuit (FIG. 8) which includes a power source and a detector to sense when the exposed bottom ends of the leads 118 and 120 contact a fluid surface to provide a level sensor for the mechanism 10. The bottoms of the probe 116 and the leads 118 and 120 are spaced so that the bottom end 116 has a minimal contact with the fluid in the cavities 22 and 32 and so that there is a minimal amount of carry-over on the outside of the probe 24 and a precise aliquot of fluid thus may be aspirated and dispensed.

The probe 24 is mounted through an aperture 124 in a slide 126. The slide 126 includes a mounting block 128 formed therewith or fixed thereto which includes a threaded bore 130 into which is inserted a spring type plunger 132 which ensures the proper orientation of the probe 24. The spring plunger 132 allows the probe 24 to move laterally and vertically if the probe 24 should be moved against a solid object to avoid damage to the probe 24 and mechanism 10. The vertical positioning of the probe 24 is maintained by a spring 134 which is screwed around a threaded portion 136 of the mounting block 128 on one end and at the opposite end around a threaded portion 138 of the probe 24. Thus, if the probe 24 should be moved against a solid object in its downward travel the probe 24 will pop up through the aperture 124 to avoid damage to the mechanism 10. Such a malfunction could occur without any fault of the mechanism 10 since the supply 14 may not move the cavities 22 into the proper position or the rotor 18 may not move the cuvettes 20 into the proper position or one of the cuvettes 20 could be blocked.

Figure 6:
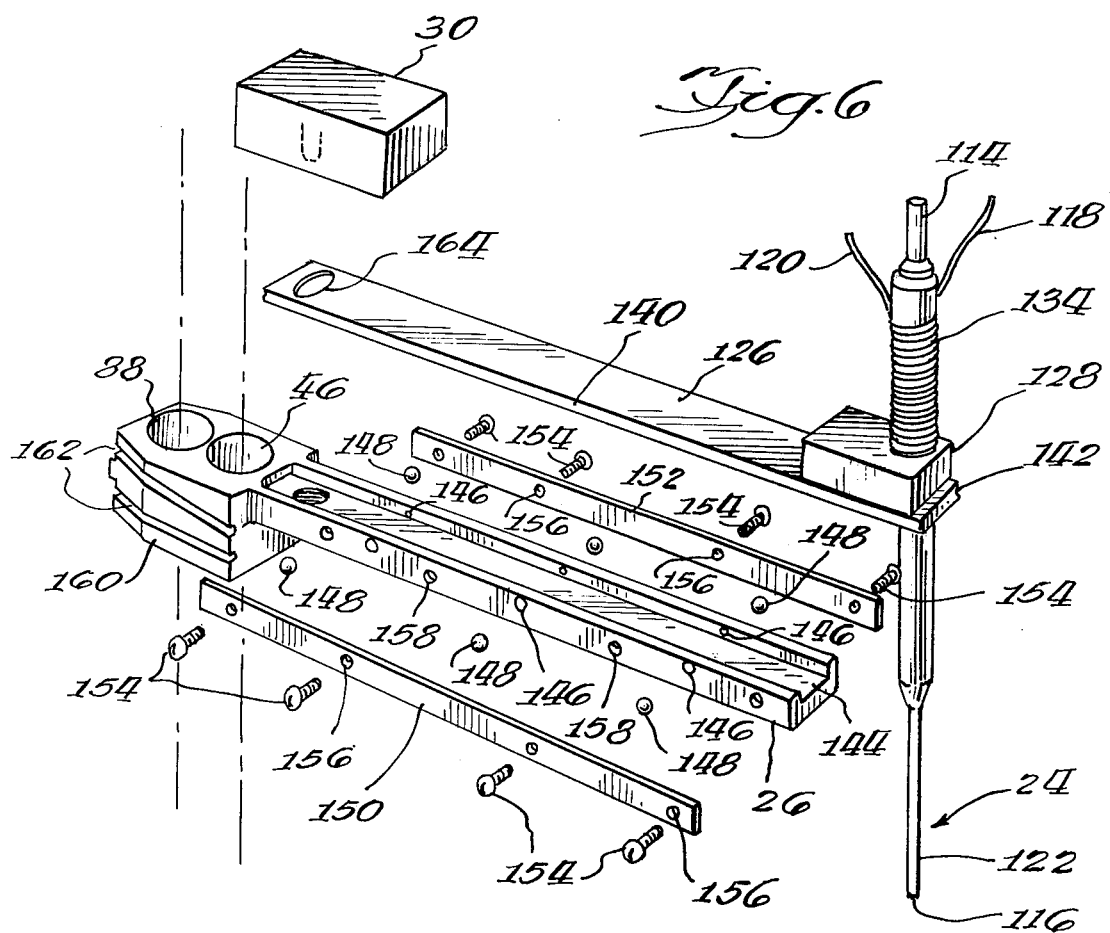
FIG. 6 is an exploded perspective view of the transfer arm and probe of FIG. 2.
Figure 5:
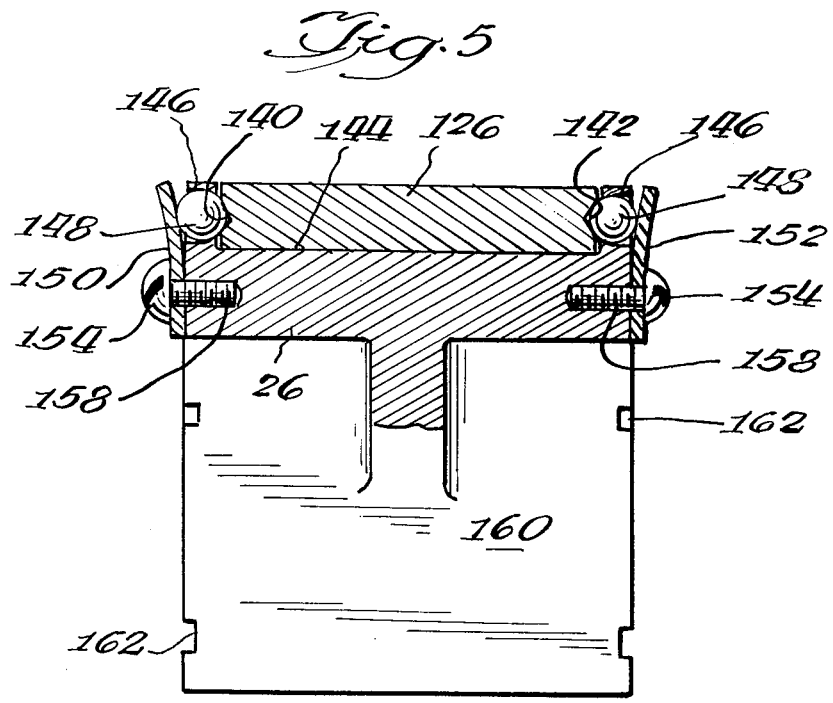
FIG. 5 is a side sectional view of the arm of the transfer mechanism taken along the line 5—5 of FIG. 2.

The probe 24 is oscillated back and forth to stir the fluids in the cuvettes 20 on the slide 126 by the motor 30. The operation of the motor 30, construction of the slide 126 and mounting on the arm 26 is best illustrated in FIGS. 5 and 6. The slide 126 includes a pair of grooves 140 and 142 in either side of the slide and extending the length thereof. The top portion of the arm 26 includes a channel 144 into which the slide 126 fits with lateral space between the sides of the channel 144 and the grooves 140 and 142. The sides of the channel 144 include a plurality of bores 146 therethrough, which have a first outer dimention and a second smaller inner dimension opening into the channel 144. The bores 146 each have a ball bearing 148 inserted into the first dimension portion thereof and partially extending into the channel 144 to engage in the respective grooves 140 and 142. The ball bearings 148 are maintained in the bores 146 by a pair of spring plates 150 and 152.

The spring plates 150 and 152 are secured to the arm 26 by a plurality of screws 154 inserted through apertures 156 in the plates 150 and 152 and into threaded bores 158. The arm 26 includes a base portion 160 in which is formed the nut passageway 46 and the bearing passageway 88. The base 160 may include grooves or slots 162 in the sidewalls thereof into which the leads for the wires 118 and 120 and the tubing 114 may be secured. The slide 126 is reciprocated in the channel 144 by the motor 30 with an eccentric drive shaft extending through an aperture or slot 164 in the plate 126.

A second embodiment of the mechanism 10 including a probe 24' is illustrated in FIG. 7. The mechanism 10 in FIG. 7 as well as the probe 24', provides the same operations as previously described. Substantially identical members will be described with the same numbers as previously utilized in FIGS. 1 through 6 with a prime to indicate minor modifications and different numerals are used for elements which have been substantially or completely changed.

The probe 24' includes a stainless steel pick up and dispensing probe 166 mounted in a non conductive sleeve 168 by a threaded fitting 170. The probe 166 includes a bottom tip 172 which has the fluid aspirating and dispensing opening therein and also serves to form one lead of a capacitive level sensing circuit described in FIG. 8. The electrical connection to the probe 166 is made by a block 174 which is welded or otherwise electrically connected to an upper end 176 of the probe 166 and includes an electrical lead (FIG. 8) connected in a conventional manner.

The upper end 176 of the probe 166 will have a fluid tubing connected thereto. The sleeve 168 is mounted in a slide 126' which is screwed or otherwise secured to a conventional ball slide 176 (only the slide portion thereof being illustrated in the Figure) which is mounted on the arm 26'. The motor 30 again has an eccentric drive shaft 180 engaged in the drive slot 164 in the slide 126'. The motor 38 rotates a drive pulley 58' by the drive belt 56. The hub 60' is secured to the pulley 58' and rotates with the pulley 58' around a pair of bearings 182 and 184 which are mounted on a non rotating hub 186 mounted to the baseplate 48.

The high helix drive shaft 28 is mounted for rotation in a pair of bearings 188 and 190 mounted on the inside of the hub 186. The bearings 182 and 188 are secured by a cap 192 screwed or otherwise secured to the hub 186. The shaft 28 is mounted in the bearings 188 and 190 by its lower end 68'. The lower end 68' of the shaft 28 is secured to the drive shaft 70 of the motor 40 by a flexible coupling 194. The coupling 194 is rotationally rigid and axially flexible with the shaft 28 to eliminate motor vibrations and binding from the operation of the mechanism 10.

The hub 60' includes a flange 196 to which is secured a code skirt 198 which extends partially or totally around the hub 60' depending upon the maximum angle of rotation through which the arm 26' will be rotated. The code skirt 198 may be read by an optical reader 200 mounted on a plate 202 on the baseplate 48. The code position reader 200 again may be utilized to verify the number of drive pulses fed to the motor 40 to ensure that the proper position has been reached by the probe 24'. The code also may be utilized as the primary position control for the arm 24' if desired.

The arm 26' includes the drive nut 44 engaged on the high helix screw 28'. The upper end of the high helix screw 28' is not engaged in the upper retainer 76'. The upper retainer 76' still includes the dowwardly depending tab 92 cooperating with the reader 90 carried by the arm 26'. The guide rod 72' is mounted in the hub 60' and retained in the retainer 76' and slidingly engaged through the bearing 86, preferably a ball bushing type of bearing, for ease of movement of the arm 26' up and down the guide rod 72'.

A second guide rod 204 has one end mounted in the hub 60' and the other end in the retainer 76'. The guide rod 204 is engaged through a passageway 206 in the arm 26', which may or may not include a bearing therein. With the two parallel guide rods 72' and 204, the upper end of the shaft 28' might cause the movement of the arm 26' to bind if the upper end was retained in the retainer 76'. The second guide rod 204 further ensures that the probe 24' is properly aligned and the mechanism 10 has the necessary life and reliability.

The lowermost position of the arm 26' is shown in phantom at 208, which is the lowest position of the arm 26'. The position 208 may be obtained either by counting the drive pulses to the motor 40, as previously described, or by one or more other optical readers mounted on the arm 26' similar to, but spaced from the reader 90 and corresponding position tabs mounted on the hub 60' (not shown).

An embodiment of a control circuit 210 of the mechanism 10 is illustrated in FIG. 8. The control circuit 210 may be a portion of the control of the analyzer 12 or may be a separate control provided with one or more of the mechanisms 10 as desired. For purposes of description only, the control 210 will be described as operating with the level sensing probe 24' with the sample mechanism 10, the probe 24' with the mechanism 10' and the probe 24 with the mechanism 10''. Generally, the analyzer 12 would be supplied with substantially identical mechanisms 10, 10' and 10'' and hence only one type of probe 24 or 24'. Further as previously described, only one mechanism 10 may be operating with the control 210.

Referring to the mechanism 10 the level sensing circuit includes an oscillator 212 which supplies a high frequency output on a pair of lines 214 and 216. There also could be a separate oscillator 212 with each of the probes 24' for the mechanisms 10 and 10'. The line 214 couples the high frequency signal through a capacitor 218 to the probe 24' on a line 220 and to a resistor 222. When the probe 24' has its tip 172 above the fluid surface 224, the current path is through the capacitor 218 and resistor 222 to ground. This current level or voltage proportional to current is sensed by a detector 226 over a line 228 coupled to the junction of the line 220 and the resistor 222. When the probe tip 172 reaches the sample fluid surface 224 in one of the cavities 22 a second current path is formed through the capacitor 218, the line 220, the probe 24' and the fluid in the cavity 22 which has a fluid resistance 230. The cavity 22 may be formed of a conductive material or may have an electronic ground closely associated therewith, which will act in the same manner as the circuit described with respect to the mechanism 10'.

By designing the resistance 222 to be of a significantly different magnitude than the fluid resistance 230, when the probe tip 172 touches the fluid surface the detector 226 will sense the current change and couple a level sensing signal to the control 210 on a line 232. The control 210 may utilize this to control the motor 40 to stop the probe tip 172 from being immersed further in the fluid or to stop the probe a precise distance below the fluid surface 224 as desired. Thus, the probe 24' may be utilized to aspirate or pick up the sample fluid in the cavity 22 without immersing the probe tip 172 completely in the fluid, without regard to the fluid level 224 in the cavity 22.

The level detecting circuit of the mechanism 10' is illustrated with the probe 24' in one of the reagent containers 32, which typically may be formed of glass or other conventional non conductive material. In this instance the high frequency signal, for example about 100 kilohertz, is coupled on the line 216 through a capacitor 234 to a resistor 236 and by a line 238 to the probe 24' and the tip 172. When the probe 24' is above the reagent surface 240, the current path is through the resistor 236 to ground which is detected on a line 242 by a detector 244. The detector 244 may be a separate detector or it could be a portion of the detector 226. When the probe tip 172 contacts the fluid surface 240 a second current path is established through the reagent fluid which has a fluid resistance 246.

The container 32; however, is made of a non conductive material such as glass and therefore acts as a capacitance 248. The containers 32 may be placed in a metallic well or against a metallic grounded surface in the reagent supply 16 to complete the circuit path. Again, the impedance value of the resistor 236 is chosen to be significantly different than the impedance provided by the fluid resistance 246 and the container capacitance 248. When the current path is established by the probe 172 contacting the fluid surface 240, the detector 244 will detect the current difference and couple a level sensing signal on a line 250 to the control 210. Again, the control 210 may insert the tip 172 as far below the surface 240 as it is desirable for the particular operation. The capacitors 218 and 234 and the AC signal prevent electrolysis of the fluids.

The mechanism 10" is illustrated with the level sensing probe 24 having the electrical leads 116 and 118. One of the leads, for instance 118, is coupled to a signal source 252 which could be identical to the oscillator 212 if desired. In this instance, the line 120 is coupled to a detector 254 which will not receive a signal when the probe 24 and the ends of the leads 118 and 120 are above the fluid surface 256. When the leads 118 and 120 contact the fluid surface 256 in the reagent container 32, the signal from the source 252 on the line 118 will be coupled across the fluid to the lead 120 and will be detected by the detector 254. The detector 254 then couples a level sensing signal over a line 258 to the control 210 indicating that the tip 116 has reached a known position with respect to the fluid surface 256, depending on the alignment with the leads 118 and 120.

The other functions of the control 210 are diagrammatically illustrated for one probe 24. The control 210 will apply the appropriate number of drive pulses to the motor 38 on a line 260 to rotate the arm and hence the probe 24 to the proper pick up position. Assuming for example, that this is one of the sample cavities 22 the control 210 will assume the probe 24 has been rotated the proper distance. The position may be verified to see that the arm 26 and hence the probe 24 are in the proper position by reading the position of the code wheel 98 by the reader 104. The control 210 after determining that the probe 24 is in the proper position above the cavity 22 located in the pick up position of the mechanism 10, then will provide drive pulses to the vertical motor 40 over a line 262 to drive the probe 24 downwardly to the fluid surface.

The level detector will generate a signal when the probe tip reaches the fluid level which is coupled to the control 210. The control then will stop the drive pulses on the line 262 with the probe tip at or slightly below the fluid surface. The control 210 will then activate a fluid motive source 264 by a line 266. The fluid motive source 264 may be a syringe drive or other fluid moving means coupled by appropriate valving to the fluid tubing 114. The syringe will be driven the appropriate distance to pick up or aspirate the proper amount of fluid into the probe passageway 108.

The dimensions of the probes 24 and 24' will be chosen so that the sample fluid volume or reagent fluid volume will be contained entirely in the passageway 108 or probe 166. This substantially eliminates any carry-over problem when the probes are washed in the probe washer 34. Once the probe 24 has aspirated the desired fluid aliquot, the control 210 will provide pulses to the motor 40 over the line 262 to drive it upwardly until the switch 90 is activated by the tab 92 indicating that the probe 24 and arm 26 are in the uppermost position. When the arm and hence the probe 24 have reached the uppermost or rotating position the control 210 then will provide the appropriate number of drive pulses on the line 260 to the motor 38 to rotate the probe 24 to the dispensing position above the cuvette 20 or other reaction vessel located in the dispensing position. The angular position again may be verified the code wheel 98.

The probe 24 then is driven downwardly to its lowermost dispensing position, which will be fixed by a switch such as the tab 96 or by the number of drive pulses applied to the vertical motor 40. The control 266 then indicates to the fluid motive source 264 that the probe 24 is in the dispense position and then the source 264 will dispense the fluid in the probe 24 and by appropriate valving also may add an amount of diluent to the sample aliquot in the cuvette 20. The control 210 will then activate the oscillating motor 30 over a line 268 to oscillate the probe 24 back and forth to stir the fluids in the cuvette 20. The control 210 will deactivate the motor 30 and then drive the probe 24 to the uppermost position by supplying the drive pulses to the motor 40.

The probe 24 then is rotated by the motor 38 to a position above the probe washer 34, where it is driven downwardly by the motor 40 into the probe washer and externally washed in the probe washer 34. The probe 24 may be internally washed by coupling a wash fluid from the source 264 through the probe passageway 108 or 166. The probe then is driven back up to its uppermost position by the motor 40 where it then is maintained in a ready position for the next cycle.

Many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. An improved pre-programmed multiple position fluid transfer mechanism comprising:
   A. an arm;
   B. shaft means movably coupled to a first end of said arm and having an axis;
   C. first drive means for moving said arm in translation relative to said shaft means and along said shaft means axis;
   D. second drive means for rotating said arm in an arcuate path around said shaft means axis; and
   E. probe means mounted on a second distal end of said arm including a fluid probe extending from said probe means and arm for picking up and dispensing fluids.

2. A fluid transfer mechanism as claimed in claim 1 including:
means for accelerating said second drive means for the first portion of movement in said path and decelerating said second drive means for the last portion of movement in said path.

3. A fluid transfer mechanism as claimed in claim 1 including:
biasing means mounting said fluid probe on said arm to bias said probe in a first position and allowing said probe to move into a second position as said probe contacts a surface other than a fluid surface.

4. A fluid transfer mechanism as claimed in claim 1 including:
said shaft means including a high helix screw coupled to said first drive means and angularly fixed to said arm to move said arm up and down along said axis when said shaft means is rotated by said first drive means.

5. A fluid transfer mechanism as claimed in claim 1 including:
said first drive means including a stepper motor for moving said arm; and
means for controlling the position of said arm and probe means on said shaft means.

6. A fluid transfer mechanism as claimed in claim 1 including:
guide means coupled to said shaft means to maintain the angular position of said arm as said arm is moved up and down said shaft means axis by said first drive means.

7. A fluid transfer mechanism as claimed in claim 6 including:
a hub coupled to said second drive means; and
said guide means including at least one post mounted on said hub at one end and extending through said arm and connected to said shaft at the other end.

8. A fluid transfer mechanism as claimed in claim 1 including:
oscillating means mounted on said arm for oscillating said probe to stir fluids in which said probe is positioned.

9. A fluid transfer mechanism as claimed in claim 8 including:
slide means mounted on said arm having said probe mounted on a distal end thereof; and
said oscillating means are coupled to the opposite end of said slide means to oscillate said slide means and probe means on said arm.

10. A fluid transfer mechanism as claimed in claim 1 including:
said probe means including level sensing means coupled thereto for sensing when said fluid probe contacts a fluid surface.

11. A fluid transfer mechanism as claimed in claim 10 including:
said level sensing means including a pair of electrical leads extending substantially parallel to a fluid opening in said fluid probe to form an electrical path through said fluid between said leads when said leads contact said fluid surface.

12. A fluid transfer mechanism as claimed in claim 10 including:
said level sensing means including a conductive metal probe coupled to electronic oscillating means to form an alternating current path through said fluid when said metal probe contacts said fluids.

13. A fluid transfer mechanism as claimed in claim 10 including:
means for accelerating said second drive means for the first portion of movement in said path and decelerating said second drive means for the last portion of movement in said path;
guide means coupled to said shaft means to maintain the angular position of said arm as said arm is moved up and down said shaft means axis by said first drive means;
means for controlling the position of said arm and probe means on said shaft; and
means for controlling the angular position of said arm and probe means.

14. A fluid transfer mechanism claimed in claim 1 including:
said second drive means including a stepper motor for rotating said arm; and
means for controlling the angular position of said arm and probe means.

15. A fluid transfer mechanism as claimed in claim 14 including:
said control means including code means fixedly rotated with said arm and means for reading said code means corresponding to the angular position of said arm.

16. A fluid transfer mechanism claimed in claim 14 including:
means for accelerating said second drive means for the first portion of movement in said path and decelerating said second drive means for the last portion of movement in said path.

17. A fluid transfer mechanism as claimed in claim 16 including:
said acceleration and deceleration means including means for changing the frequency of drive pulses supplied to said stepper motor.

18. A fluid transfer mechanism as claimed in claim 14 including:
said first drive means including a stepper motor for moving said arm; and
means for controlling the position of said arm and probe means on said shaft means.

19. A fluid transfer mechanism as claimed in claim 18 including:
counter means for counting the number of drive pulses coupled to each of said drive means corresponding to the positions of said arm.

* * * * *